United States Patent [19]

Smuda et al.

[11] Patent Number: 4,997,989
[45] Date of Patent: Mar. 5, 1991

[54] TERT-BUTYLALKYNOLS

[75] Inventors: Hubert Smuda, Heidelberg; Wolfgang Rohr, Wachenheim, both of Fed. Rep. of Germany

[73] Assignee: BASF Aktiengesellschaft, Ludwigshafen, Fed. Rep. of Germany

[21] Appl. No.: 293,447

[22] Filed: Jan. 4, 1989

[51] Int. Cl.$^5$ ............................................ C07C 41/00
[52] U.S. Cl. ..................................... 568/649; 568/637; 568/638; 568/640; 568/641; 568/643; 568/654
[58] Field of Search ............... 568/637, 638, 641, 643, 568/648, 649, 636, 640, 644, 645, 654

[56] References Cited

U.S. PATENT DOCUMENTS 3,513,198 5/1970 O'Brien et al.
4,380,546 4/1983 Sauter et al.

FOREIGN PATENT DOCUMENTS 1069350 5/1962 United Kingdom.
1102639 2/1968 United Kingdom.

OTHER PUBLICATIONS

CA 77 61434f 1972.
CA 78 71594t 1973.
CA 81 67175b 1974.
Pourcelot & Cadiot, Bull. Soc. Chim., France, pp. 3016, 3024 (1966).
McKillop et al., Tetrahedron, vol. 30, p. 1379 (1974).
Dehmlow, Phase Transfer Catalysis In Organic Synthesis, Verlag Chemie, Weinheim, pp. 36-37, (1980).

*Primary Examiner*—Bruce Gray
*Attorney, Agent, or Firm*—Keil & Weinkauf

[57] ABSTRACT

Novel tert-butylalkynols of the formula (I)

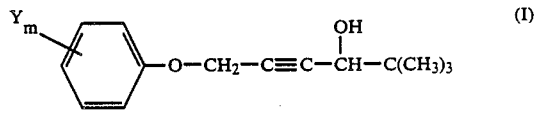

where Y is hydrogen, halogen, $C_1$-$C_4$-alkyl, $C_1$-$C_4$-alkoxy, $C_1$-$C_4$-haloalkyl, aryl, aryloxy or benzyl and m is an integer from 1 to 3, and the individual groups Y may be identical or different when m>1, and a process for their preparation are described.

5 Claims, No Drawings

TERT-BUTYLALKYNOLS

The present invention relates to novel tertbutylalkynols of the formula (I)

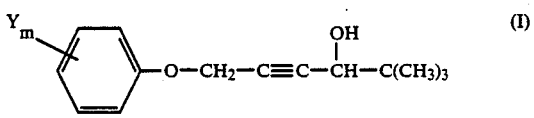

where Y is hydrogen, halogen, $C_1$-$C_4$-alkyl, $C_1$-$C_4$-alkoxy, $C_1$-$C_4$-haloalkyl, aryl, aryloxy or benzyl and m is an integer from 1 to 3, and the individual groups Y may be identical or different when $m > 1$, and a process for their preparation.

The novel tert-butylalkynols are starting materials for the preparation of 1,2,4-triazolyl-substituted substituted fungicides, as described in DE-A 30 19 049 which corresponds to U.S. Pat. No. 4,380,546 and EP-B 150 404. However, they have not been prepared satisfactorily to date.

For example, these compounds can be prepared by the conventional methods (cf. DE-A 30 19 049 and EP-B 150 404) only in unsatisfactory yields or only by a complicated preparation procedure. Owing to their costefficiency, these processes are therefore not very suitable for industrial use.

It is an object of the present invention to make these active ingredients more readily available by providing novel starting materials.

We have found that this object is achieved by tert-butylalkynols of the general formula (I)

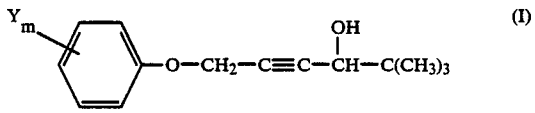

where Y is hydrogen, halogen, $C_1$-$C_4$-alkyl, $C_1$-$C_4$-alkoxy, $C_1$-$C_4$-haloalkyl, aryl, aryloxy or benzyl and m is an integer from 1 to 3, and the individual groups Y may be identical or different when $m > 1$.

We have also found a process for the preparation of tert-butylalkynols of the formula (I)

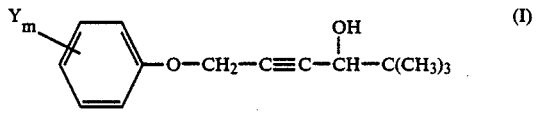

where Y is hydrogen, halogen, $C_1$-$C_4$-alkyl, $C_1$-$C_4$-alkoxy, $C_1$-$C_4$-haloalkyl, aryl, aryloxy or benzyl and m is an integer from 1 to 3, and the individual groups Y may be identical or different when $m > 1$, wherein a phenyl propargyl ether of the formula (II)

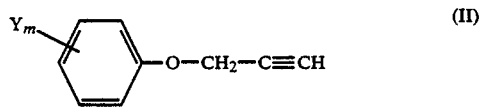

is reacted with 2,2-dimethylpropanal in the presence of a mineral base in a polar aprotic solvent to give a tert-butylalkynol (I).

The phenoxy radical is preferably substituted by $Y_m$ as follows: hydrogen, 2-fluoro, 3-fluoro, 4-fluoro, 2-chloro, 3-chloro, 4-chloro, 4-bromo, 2,4-dichloro, 2,4,6-trichloro, 3,4-dichloro, 3,5-dichloro, 2-chloro-4-phenyl, 2-methyl-4-chloro, 2-methyl, 3-methyl, 4-methyl, 3-tert-butyl, 4-tert-butyl, 2-methoxy, 3-methoxy, 4-methoxy, 3,5-dimethoxy, 3-n-butoxy, 4-n-butoxy, 2-methoxy-4-methyl, 3-trifluoromethyl, 4-trifluoromethyl or 4-phenoxy.

m is particularly preferably 1 and Y is particularly preferably hydrogen, 4-methoxy, 2-chloro, 3-chloro, 4-chloro, 4-tert-butyl, 2-methyl or 3-methyl.

The novel tert-butylalkynols I are advantageously prepared by reacting a phenyl propargyl ether of the formula (II)

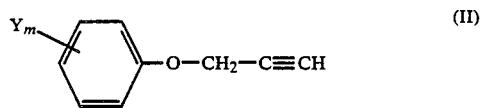

with 2,2-dimethylpropanal in the presence of a base suitable for Favorskii reactions, in a polar aprotic solvent, to give the tert-butylalkynols (I).

The phenyl propargyl ethers (II) used as starting materials are known per se (cf. for example Netherlands Applications 6 614 925 of Apr. 24, 1967 or 6 612 645 of Mar. 9, 1966) or can be prepared by known methods (for example according to Pourcelot and Cadiot: Bull. Soc. Chim. Fr. 1966, 3016, 3024; McKillop et al.: Tetrahedron 30, (1974), 1379), for example by reacting an unsubstituted or substituted phenol with a propargyl derivative $XCH_2C \equiv CH$, where X is a leaving group, in the presence of a base in accordance with the following equation:

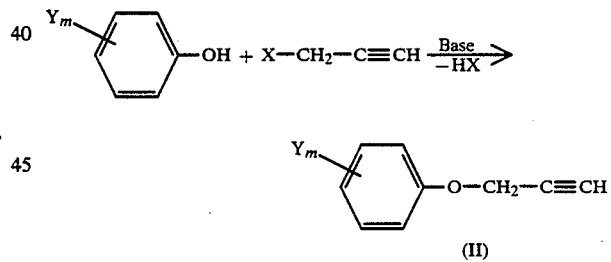

The reaction of the phenyl propargyl ether (II) with 2,2-dimethylpropanal takes place as a Favorskii reaction (cf. Merck Index, 9th Edition, ONR-29, 1976, and Houben-Weyl, Methoden der organischen Chemie, Vol. V/2a, 1977, 509–519, and the literature cited therein) in accordance with the following equation:

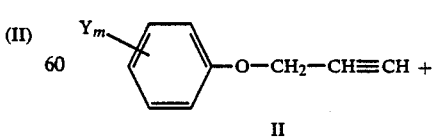

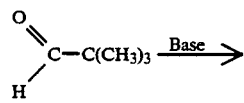

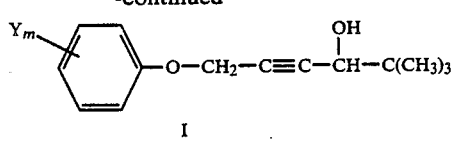

I

Examples of suitable bases for carrying out the reaction are Grignard reagents, organolithium compounds or alkali metal hydroxides, in particular potassium hydroxide. Because it is substantially less sensitive to hydrolysis compared with Grignard reagents or organolithium compounds, potassium hydroxide is particularly preferably used. Furthermore, potassium hydroxide as the base has the advantage of being effective even in catalytic amounts.

The amount of potassium hydroxide used in the reaction is not critical. Accordingly, the potassium hydroxide can be used in excess, in an equivalent amount or in a catalytic amount. The potassium hydroxide is preferably used in amounts of from 0.01 to 1.0, in particular from 0.5 to 1.0, equivalent, based on the propargyl ether to be reacted.

0.5–1.0 mole of propargyl ether can be used per mole of 2,2-dimethylpropanal, but equimolar amounts are preferred.

The reaction can be carried out in a conventional polar aprotic organic solvent. Ethers, e.g. diethyl ether, glycol dimethyl ether, triglycol dimethyl ether, tetrahydropyran and, in particular, tetrahydrofuran, are preferred. The reaction temperature can be from 0° to 80° C., preferably from 20° to 60° C.

Working up is advantageously carried out by neutralizing the mixture and extracting it with water and with a water-immiscible organic solvent, e.g. toluene. After the extraction solutions have been evaporated down, the crude products can be further purified by suitable methods, such as column chromatography.

The novel tert-butylalkynols (I) serve as intermediates for the preparation of azolyl active ingredients, such as the 1,2,4-triazol-1-yl derivatives described in DE-A 30 19 049.

For this purpose, the novel tert-butylalkynols (I) are converted into the phenyl alkynyl ketones (IV) by oxidation with a conventional oxidizing agent, for example sodium dichromate/sulfuric acid, manganese dioxide or nickel peroxide, or electrochemically by anodic oxidation. The subsequent catalytic hydrogenation of the triple bond, for example by means of a palladium catalyst in methanol, gives the phenoxyalkyl ketones (III).

The reaction sequence is shown in the following scheme:

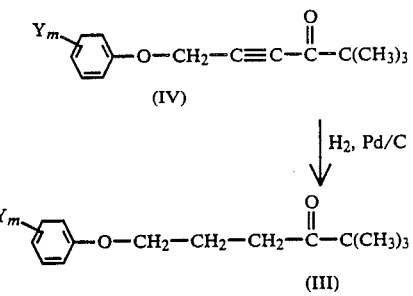

The azolyl active ingredients can be synthesized from the phenoxyalkyl ketones (III) in a conventional manner, as described in EP-B 150 404.

EXAMPLES

The propargyl ethers (II) required for the preparation of the tert-butylalkynols of Examples 1 to 12 were prepared by the processes of Pourcelot et al. (Bull. Soc. Chim. Fr. 1966, 3016, 3024) and McKillop et al. (Tetrahedron 30 (1974), 1379). General method for the preparation of tert-butylalkynols One equivalent of a phenyl propargyl ether II in 5 times the volume of tetrahydrofuran was initially taken. One equivalent of solid potassium hydroxide was added, after which 1.2 equivalents of pivalaldehyde (2,2-dimethylpropanal) were added dropwise. After the total amount of pivalaldehyde had been added, the mixture was stirred at 50° C. until HPLC analysis (high pressure liquid chromatography) of a sample indicated that all of the phenyl propargyl ether had been consumed.

To work up the mixture, undissolved potassium hydroxide was filtered off, 5% by weight of water were added to the filtrate and excess alkali was neutralized with 10% strength by weight hydrochloric acid. Toluene was added to the mixture, the water phase was separated off and the toluene phase was extracted with water. The toluene phase was dried over sodium sulfate, after which the organic solvents were evaporated off. The tert-butylalkynols were obtained as yellow oils, which decomposed when an attempt was made to distill them.

The tert-butylalkynols shown in Table 1 below were obtained by this method.

TABLE 1

I

| Example | $Y_m$ | Yield % of theory | $^1$H-NMR (CDCl$_3$) (a) $^{13}$C-NMR (CDCl$_3$) (a) |
|---|---|---|---|
| 1 | H | 92 | δ = 7.32(m; 2H); 7.0(m; 3H); 4.78(s; 2H); 4.05(d; 1H); 1.8(d; OH); 0.92(s; 9H) |
|   |   |   | δ = 157, 129 (2×C) 121, 115 (2×C), 87, 80, 71, 56, 36, 25 (3×C) |
| 2 | Cl | 69 | δ = 7.1(d; 2H); 6.95(d; 2H); 4.75(s; 2H); 4.05(s; 1H); 2.4(s; OH); 0.95(s; 9H) |
| 3 | 4-C(CH$_3$)$_3$ | 54 | δ = 7.3(d; 2H); 6.9(d; 2H); 4.75(s; 2H); 4.05(s; 1H); 1.95(s broad; OH); 1.25(s; 9H); 0.95(s; 9H); |
|   |   |   | δ = 155.4; 144.1; 129.0 (2×C) 114.7 (2×C), 87.2; 80.7; 71.2; 56.2; 35.8; 34.1; 31.5 (3×C); 29.7 (3×C) |
| 4 | 2-CH$_3$ | 78 | δ = 7.1(m; 2H); 6.85(m; 2H); 4.7(s; 2H); 4.0(s; 1H); 2.2(s; 3H); 0.95(s; 9H) |

TABLE 1-continued $$Y_m\text{-}C_6H_3\text{-}O\text{-}CH_2\text{-}C\equiv C\text{-}CH(OH)\text{-}C(CH_3)_3 \quad \text{I}$$

| Example | $Y_m$ | Yield % of theory | $^1$H-NMR (CDCl$_3$) (a)<br>$^{13}$C-NMR (CDCl$_3$) (a) |
|---|---|---|---|
| | | | δ = 156.1; 130.9; 127.5; 126.7; 121.5; 112.6; 87.3; 81.0; 71.3; 56.5; 35.8; 25.3; 16.0 |
| 5 | 3-CH$_3$ | 77 (b) | δ = 7.1(t; 1H); 6.75(d; 3H); 4.68(s; 2H); 4.00(s; 1H); 2.4(s broad; OH); 2.3(s; 3H); 0.95(s; 9H) |
| | | | δ = 157.9; 139.3; 129.2; 122.5; 116.3; 112.4; 112.1; 87.5; 80.9; 71.3; 56.2; 35.8; 28.8; 21.4 |
| 6 | 4-CH$_3$ | 72 | δ = 7.0(d; 2H); 6.8(d; H); 4.6(s; 2H); 4.0(s; 1H); 2.3(S; 3H); 1.0(s; 9H); |
| | | | δ = 156, 131, 130(2×C), 115(2 ×C), 88, 81, 71, 57, 36, 25(3×C) |
| 7 | 4-CH$_3$ | 76 | δ = 6.8(dd; 4H); 4.6(s; 2H); 4.0(s; 1H); 3.65(s; 3H); 2.5(s broad; OH); 0.95(s; 3H) |
| | | | δ = 155, 152, 117 (2×C); 115 (2×C); 88, 81, 71, 57, 56, 36, 25 (3×C) |
| 8 | 2-OCH$_3$ | 85 | δ = 6.85(m; 4H); 4.7(s; 2H); 3.95(s; 1H); 3.8(s; 3H); 0.9(s; 9H) |
| | | | δ = 151, 148, 123, 121, 116, 113, 88, 81, 71, 58, 56, 36, 25 (3×C) |
| 9 | 3-F | 77 | δ = 7.2(m; 1H); 6.7(m; 4H); 4.7(s; 2H); 4.0(s; 1H); 0.95(s; 9H) |
| | | | δ = 163.6(d; $J_{C-F}$=245.7Hz); 159(d); 130, 111, 108, 103; 88, 80, 71, 57, 36, 25(3×C) |
| 10 | 4-F | 93 | δ = 7.0(d; 2H); 6.9(d; 2H); 4.7(s; 2H) 4.0(s; 1H); 2.9(s broad, OH); 0.9(s; 9H) |
| | | | δ = 158(d; $J_{C-F}$=239.1Hz); 154, 117(2×C); 116(2×C); 88, 81, 71, 57, 36, 25(3×C) |
| 11 | 2,4-F$_2$ | 85 | δ = 7.05(m; 1H); 6.8(m; 2H); 4.75(s; 2H); 4.0(s; 1H); 0.9(s; 9H) |
| | | | δ = 157(d; $J_{C-F}$=243.7Hz); 154(d; $J_{C-F}$=250.4Hz); 142, 119, 111, 105 (d, d); 89, 80, 71, 59, 36, 25(3×C) |
| 12 | 3-CF$_3$ | 91 | δ = 7.4(m; 1H); 7.2(m; 3H); 4.7(s; 2H); 4.0(s, 1H); 2.6(broad, OH); 0.9(s; 9H) |
| | | | δ = 158; 132(m; $J_{C-F}$=32.8Hz); 130; 124(m; $J_{C-F}$=272.1Hz); 119, 118; 112; 88; 80; 72; 57; 36; 29(3×C). |

(a) The chemical shift δ is based on the standard tetramethylsilane (TMS) = 0
(b) CH analysis: calculated: C 77.55; H 8.68; found: C 77.30; H 8.50

EXAMPLES OF SUBSEQUENT STAGES

Preparation of 2,2-dimethyl-6-phenoxyhex-4-yn-3-one 4.4 g (0.02 mole) of 2,2-dimethyl-6-phenoxyhex-4-yn-3-ol were dissolved in 10 ml of acetone, after which a solution of 3 g of K$_2$Cr$_2$O$_7$ and 7 g of concentrated H$_2$SO$_4$ in 10 ml of water was added dropwise. After HPLC analysis of a sample had indicated complete conversion, the reaction solution was extracted with methylene chloride. The organic phase was separated off, washed with water, dried over Na$_2$SO$_4$, filtered and evaporated down. 2.6 g (60% of theory) of a yellow oil were obtained. $^1$H—NMR (CDCl$_3$) δ=7.25 (m; 2H); 6.9 (m; 3H); 4.8 (s; 2H); $^{13}$C—NMR (CDCl$_3$) δ=193, 157, 130 (2×C), 122, 115 (2×C), 88, 84, 56, 44, 26 (3×C).

IR: 2971, 2200, 1674, 1599, 1589, 1235, 1213, 1141, 1039, 754, cm$^{-1}$.

Catalytic hydrogenation of 2,2-dimethyl-6-phenoxyhex-4-yn-3-one

In a 4 l flask connected to a hydrogenation apparatus, 2 moles of crude 2,2-dimethyl-6-phenoxyhex-4-yn-3-one were dissolved in 1.8 l of methanol and 20 g of hydrogenation catalyst (10% of palladium on active carbon) were added. The apparatus was evacuated, after which the gas space was filled with hydrogen and hydrogenation was started at room temperature while stirring. The reaction solution heated up to 35°–40° C. as a result of the heat of hydrogenation generated. After 103 l (4 moles) of hydrogen had been absorbed, absorption of H$_2$ ceased. Residual hydrogen was blown out with nitrogen. The mixture was filtered off from the catalyst and evaporated down, and the crude 2,2-dimethyl-6-phenoxy-hexan-3-one was distilled under reduced pressure. bp.: 140° C.:1.0, yield: 89% of theory. $^1$H—NMR (CDCl$_3$) δ=7.2 (m; 2H); 6.9 (m; 3H); 3.95 (dd; 2H); 2.65 (dd; 2H); 2.0 (qt; 2H); 1.12 (s; 9H) $^{13}$C—NMR (CDCl$_3$: δ=214, 159, 129 (2×C), 121, 115 (2×C), 67, 34, 26, 24.

We claim:

1. A tert-butylalkynol of the formula (I)

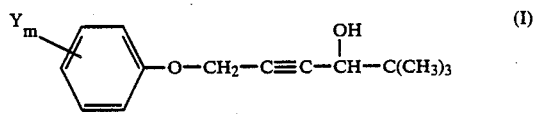

where Y is hydrogen, halogen, C$_1$–C$_4$-alkyl, C$_1$–C$_4$-alkoxy, C$_1$–C$_4$-haloalkyl, aryl, aryloxy or benzyl and m is an integer from 1 to 3, and the individual groups Y may be identical or different when m>1.

2. A tert-butylalkynol of the formula (I), as defined in claim 1, wherein Y is hydrogen, methoxy, chloro, fluoro, t-butyl or methyl and m is 1.

3. A tert-butylalkynol of the formula (I) as defined in claim 1, where Y is hydrogen, 4-methoxy, 2-chloro, 3-chloro, 4-chloro, 4-tert-butyl, 2-methyl or 3-methyl and m is 1.

4. A tert-butylalkynol of the formula (I) as defined in claim 1, wherein m is 2 and Y is fluoro, the phenoxy ring of said formula (I) being 2,4-difluoro substituted.

5. A tert-butylakynol of the formula (I) as defined in claim 3, wherein Y is hydrogen.

UNITED STATES PATENT AND TRADEMARK OFFICE
CERTIFICATE OF CORRECTION

PATENT NO. : 4,997,989

DATED : March 5, 1991

INVENTOR(S) : Hubert SMUDA et al.

It is certified that error appears in the above-identified patent and that said Letters Patent is hereby corrected as shown below:

On the title page please insert the following:

[30] --Foreign Application Priority Data

January 8, 1988...Federal Republic of Germany...3800306--

Signed and Sealed this

Twenty-eighth Day of July, 1992

Attest:

DOUGLAS B. COMER

*Attesting Officer*  *Acting Commissioner of Patents and Trademarks*